United States Patent [19]

Poindexter et al.

[11] Patent Number: 5,285,006
[45] Date of Patent: Feb. 8, 1994

[54] COMPRESSOR FOULING INHIBITION IN VINYL ACETATE PRODUCTION UNITS

[75] Inventors: Michael K. Poindexter, Sugar Land; Vincent E. Lewis, Missouri City, both of Tex.

[73] Assignee: Nalco Chemical Company, Naperville, Ill.

[21] Appl. No.: 904,968

[22] Filed: Jun. 26, 1992

[51] Int. Cl.⁵ .............................................. C07C 67/48
[52] U.S. Cl. ........................................ 560/248; 203/8
[58] Field of Search ............................. 560/248; 203/8

[56] References Cited

U.S. PATENT DOCUMENTS 4,021,476  5/1977  Harbuck ............................. 260/497
4,195,168  3/1980  Bobbin ............................... 528/495

Primary Examiner—Jose G. Dees
Assistant Examiner—Joseph M. Conrad
Attorney, Agent, or Firm—Joan I. Norek; Robert A. Miller; Joseph B. Barrett

[57] ABSTRACT

In a method for reducing the fouling of a compressor of a vinyl acetate production unit having a light ends stream feed, a hindered phenol is added to the compressor feed. The method retards the loss of compressor efficiency with run time and increases the run time before clean-out is required. The hindered phenol is added in a dosage amount effective for reducing the fouling of the compressor.

2 Claims, 1 Drawing Sheet

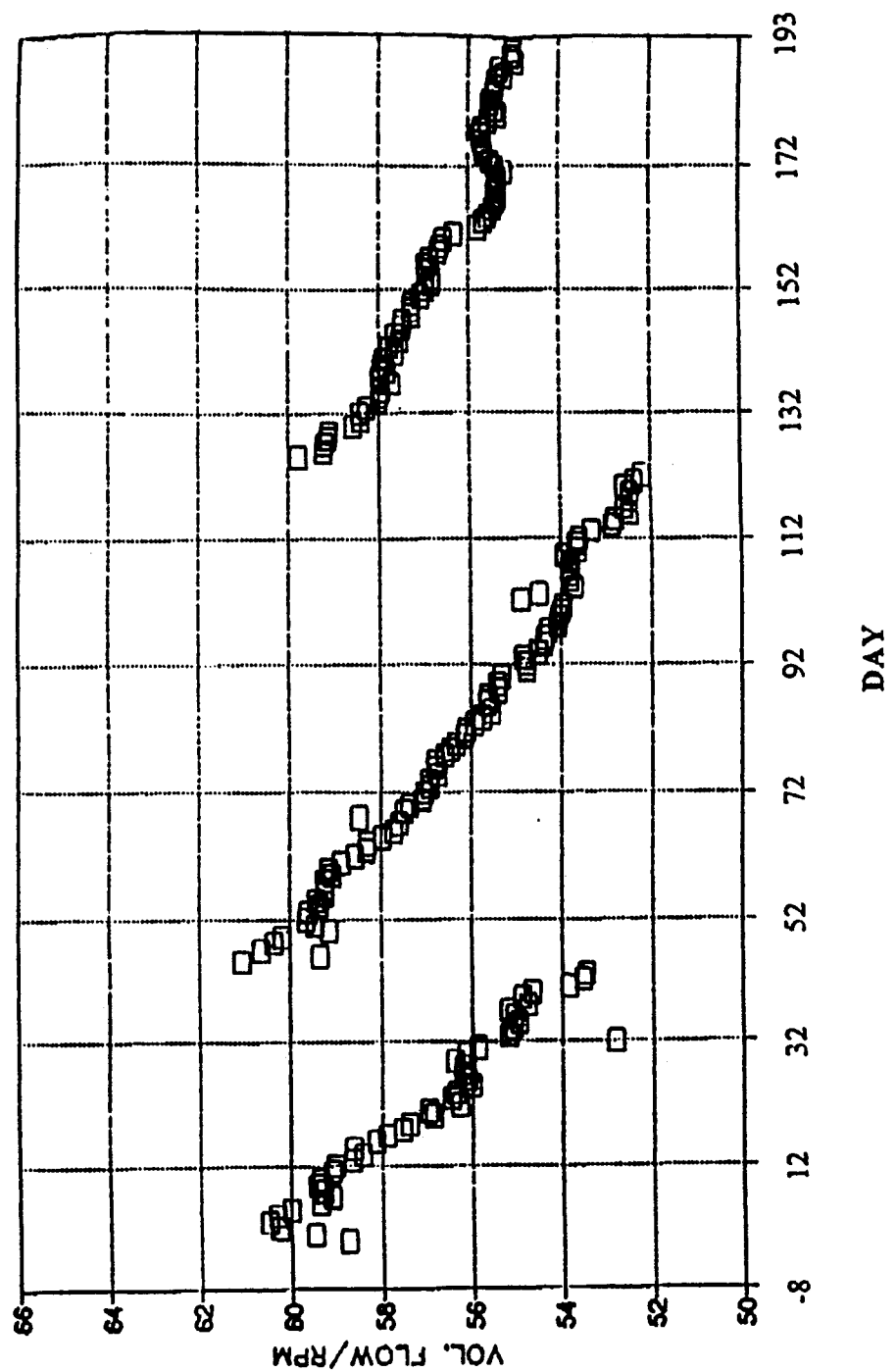

COMPRESSOR FOULING INHIBITION IN VINYL ACETATE PRODUCTION UNITS

TECHNICAL FIELD OF THE INVENTION

The present invention is in the technical field of the inhibition of fouling in a light ends stream compressor used for vinyl acetate production.

BACKGROUND OF THE INVENTION

Vinyl acetate is an ethylenically unsaturated monomer used for the production of various polyvinyl resins. It is stabilized against premature polymerization by inhibitors such as hydroquinone and diphenylamine. Such inhibitors are routinely added to vinyl acetate after production, maintained in the vinyl acetate during storage, shipping and the like, and removed prior to, or overcome during, polymerization of vinyl acetate to produce the desired resin.

Vinyl acetate is commonly produced commercially by vapor-phase reaction of ethylene and acetic acid with a palladium-based catalyst, such as a potassium or sodium acetate supported palladium catalyst system. For instance, a vapor-phase mixture of ethylene, acetic acid and oxygen is formed by passing ethylene through an evaporator containing acetic acid, and then it is passed over a fixed-bed catalyst, at elevated pressure and temperature, exiting therefrom as a product mixture. Such product mixture is typically comprised of the vinyl acetate product, ethylene, acetic acid, oxygen, and by-products/impurities. The vapor-phase product mixture is cooled by a heat exchanger(s), resulting in a vapor-liquid stream. Of the product mixture constituents, the acetic acid raw material and the vinyl acetate product have relatively high boiling points, and thus comprise the major portion of the liquid of the vapor-liquid stream, while the ethylene, oxygen, and carbon dioxide comprise the major portion of the vapor of the vapor-liquid stream.

Such vapor-liquid stream is fractionated and purified through a series of columns and washes to recover a product-quality vinyl acetate fraction and unreacted raw materials for recycling. In more detail, the vapor-liquid stream is fractionated in a column in which vinyl acetate and unreacted acetic acid (the crude vinyl acetate product) are collected as liquids at the bottom, while the vapor phase, the "light ends" or "overhead", are collected at the top. As noted above, the major portion of the vapor, and thus the light ends stream, is ethylene, oxygen and carbon dioxide. Some small amount of acetic acid may go out the top during this fractionation. If it does, then some vinyl acetate will also go out the top because vinyl acetate has a lower boiling point than acetic acid. The presence of acetic acid in the light ends stream is itself of little concern, but optimization of production requires the optimization of vinyl acetate collected at the bottom. Therefore production facilities and parameters are designed to minimize the amount of vinyl acetate in the light ends, and therefore the amount of acetic acid therein.

The light ends stream contains unreacted ethylene for recycling back to the evaporator. The light ends stream is processed through a series of wash columns to remove various by-products and then is sent to a compressor(s) to prepare the unreacted materials for reentry to the evaporator. The light ends stream is at least partially liquified by the compressor, which is referred to at times herein as the "light ends stream compressor".

Both vinyl acetate and ethylene, one of its raw material precursors, are unsaturated monomers capable of undergoing addition polymerization through their carbon-carbon double bonds. Addition polymerization may be initiated by free radicals or ions. Free radicals can be generated by the action of ultraviolet light, X-rays, heat, peroxides, oxygen, diazo compounds, and other means. Once initiated, an addition polymerization normally propagates itself by a chain-reaction mechanism, whereby polymer molecules comprised of thousands of monomer ("mer") units may be formed in a few seconds or less. The polymerization chain-reaction for a given polymer molecule is terminated when its growing end, which is itself a free radical, reacts and combines with another free radical, rather than a monomer molecule. Termination may also occur when a labile hydrogen is abstracted.

The vinyl acetate monomer is, like many ethylenically-unsaturated monomers, a volatile liquid at ambient room temperature and atmospheric pressure, and has a melting point of about $-93°$ C. The ethylene raw material is a vapor at ambient room temperature and atmospheric pressure, and has a melting point of $-169°$ C. Polymerization products of either generally would be solids at ambient room temperature and atmospheric pressure.

Formation of polymeric material in a light ends stream compressor will foul the compressor. Compressor fouling reduces compressor efficiency, and thus its production rate. Compressor fouling eventually requires that the compressor be shut down for cleaning, typically requiring the entire vinyl acetate production unit to be shut down, at least for some time period. Thus compressor fouling inevitably leads to lost production and increased maintenance costs. Fouling is caused by the presence of solid materials that coat the compressor blades and/or casing. Although solid material foulants may, to some extent, be introduced into the compressor by other means, analysis of such foulants has in the past revealed that they are comprised mostly of organic polymeric material. The major source of such foulants in such a compressor hence is the formation of polymeric materials from the unsaturated constituents of the light ends stream.

It is an object of the present invention to provide a method of inhibiting or reducing the fouling of a light ends stream compressor. It is an object of the present invention to provide a method for treating the light ends stream or compressor feed so as to retard the loss of compressor efficiency with run time by inhibiting or reducing the fouling of the light ends stream compressor. It is an object of the present invention to provide a method whereby the run time of a light ends stream compressor before clean-out is required is increased by inhibiting or reducing the fouling of the compressor. These and other objects of the invention are described in more detail below.

BRIEF DESCRIPTION OF THE DRAWINGS

FIG. 1 is a plot of compressor flow rate, in terms of thousand standard cubic feet per hour ("MSCFH") per revolution per minute ("RPM") versus time, for a light ends compressor during a time period both without treatment by the present invention and then with such treatment.

DISCLOSURE OF THE INVENTION

The present invention provides a process or method for inhibiting or reducing the fouling in a light ends stream compressor of a vinyl acetate production system comprising adding to the light ends streams, an amount of a hindered phenol effective to inhibit or reduce compressor fouling. Such hindered phenol is preferably added to the light ends stream after it is washed and upstream of the point at which it is fed to the compressor. In such embodiment the hindered phenol is added to the compressor feed.

PREFERRED EMBODIMENTS OF THE INVENTION

The effluent of a light ends stream compressor, or at least a major portion thereof, is ultimately recycled back to the evaporator, and the vapor-phase stream therefrom is fed to the catalyst bed. Any chemical species that could carry over to, and contaminate, the catalyst bed must be excluded from the light ends stream. Chemical species that contain nitrogen, sulfur, phosphorus, halogens, or metals are considered particularly undesirable because of the damage such species could cause to the catalyst bed. The present anti-foulant treatment for the compressor advantageously does not contain any such species. The hindered phenol itself is comprised solely of carbon, hydrogen and oxygen. The hindered phenol generally cannot be carried over to the catalyst bed because it is a nonvolatile species, having only a negligible vapor pressure, as discussed in more detail below. It will be carried with the compressor feed stream through the compressor. If a vehicle is employed for the hindered phenol, in preferred embodiment it is acetic acid, which of course is a component of the vapor-phase catalyst bed feed stream. In another embodiment, the hindered phenol may be charged neat to the light ends stream upstream of the compressor.

The hindered phenol is added to the compressor feed in an amount effective to reduce compressor fouling. One measure of reduced compressor fouling is the retardation of loss of compressor efficiency over its running period. In an embodiment of the present invention, the hindered phenol is added to the compressor feed in an amount effective to retard the loss of compressor efficiency. One measure of reduced compressor fouling is an increase in the time a compressor can run without requiring clean-out maintenance. In an embodiment of the present invention, the hindered phenol is added to the compressor feed in an amount effective to increase the compressor run, that is, the time a compressor can run without requiring clean-out maintenance.

In preferred embodiment, the hindered phenol is added to the compressor feed at a dosage of from about 1 ppm to about 500 ppm, and in another preferred embodiment at a dosage of from about 5 ppm to about 220 ppm. In another preferred embodiment, the hindered phenol is added to the compressor feed at a dosage of from about 10 ppm to about 100 ppm. By "ppm" is meant one part by weight of hindered phenol actives per million parts by weight of compressor feed. By "compressor feed" is meant the light ends stream as directly fed to the compressor, after any washing or other processing to remove by-products therefrom. It is believed that the hindered phenol will provide effective anti-fouling activity in typical light ends stream compressors when added to the feed stream at a dosage of from about 5 to about 100 ppm. The present method is believed effective for any other compressor that processes like type of streams.

The efficiency of such a compressor can be measured in terms of its adiabatic efficiency. The adiabatic efficiency of a compressor is the ratio of the work required to compress a gas adiabatically (without loss or gain of heat) to the work actually done by the compressor piston or impeller. The adiabatic efficiency of a compressor can be expressed as a percentage by the following formula:

$$\frac{\text{The Work Required To Compress A Gas Adiabatically}}{\text{The Work Actually Done By The Compressor Piston Or Impeller}} \times 100$$

By hindered phenol is meant herein a phenol that is sterically hindered by virtue of aromatic ring substitution at one or both of the ortho positions (ortho to the phenol's hydroxyl substituent). Such hindered phenol is one having a 2- or 6-position substituent or combinations of substituents that provide a spatial arrangement of atoms sufficient to hinder the —OH radical at the one position. In preferred embodiment, the structure of such hindered phenol is of the Formula I:

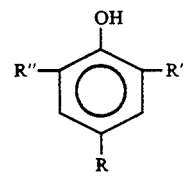

Formula I wherein R' is a linear or branched chain alkyl having at least 3 carbons and mixtures thereof, R" is hydrogen or a linear or branched alkyl and mixtures thereof, provided that together R' and R" be comprised of no more than about 12 carbons, and R is hydrogen or linear or branched, saturated or unsaturated alkyl having from one to about 28 carbon atoms and mixtures thereof. In this embodiment, the hindered phenol may have one or two ortho-position substituents, and may or may not have a para-position substituent; when it has two ortho-position substituents, one of them must have at least 3 carbons, and the other may have as few as 1 carbon. An alkyl substituent(s) at an ortho-position generally is a saturated alkyl. In more preferred embodiment, both R' and R" are alkyls each having at least about 3 carbons and mixtures thereof. In another preferred embodiment, R' and R" together contain no more than about 10 carbons. In another preferred embodiment, R is an alkyl having from about 1 to about 22 carbons and mixtures thereof, and in more preferred embodiment from about 1 to about 22 carbons and mixtures thereof, and in even more preferred embodiment from about 6 to about 22 carbons and mixtures thereof. In any of these preferred embodiments, a further preferred embodiment thereof is when an alkyl substituent(s) at the ortho-position is a branched alkyl, and preferably is branched at its 1- or benzylic-position.

In preferred embodiment, R' and R" are independently (iso)propyl, (iso/tert)butyl, or mixtures thereof. In another preferred embodiment, R is a nonyl isomer. In another preferred embodiment, R' and R" are independently a linear or branched chain alkyl having from about 3 to about 4 carbons and mixtures thereof, and R is a linear or branched, saturated or unsaturated alkyl having from about 6 to about 12 carbon atoms and mixtures thereof.

A preferred specific hindered phenol is 2,6-di-tert-butyl-4-nonylphenol.

In other preferred embodiments, the para-position may be substituted with alkyl radicals derived from fatty acids, including: unbranched saturated alkyls such as butyric, caproic, caprylic, capric, lauric, myristic, palmitic, stearic, arachidic, behenic, lignoceric, cerotic, and montanic; branched saturated alkyls such isovaleric and tuberculostearic; monoenoic alkyls such as caproleic, myristoleic, palmitoleic, petroselinic, oleic, and erucic; dienioc alkyls such as stillingic and linoleic; trienoic alkyls such as hiragonic, linolenic and eleostearic, and alkyls of more unusual structures.

In preferred embodiment, the hindered phenol has a low vapor pressure, which preferably is less than about 2.5 mm Hg at 100° F., and more preferably is less than about 2.5 mm Hg at 135° F.

EXAMPLE 1

The antifouling performance was demonstrated by the addition of 2,6-di-tert-butyl-4-nonyl phenol to a light ends stream compressor of a commercial vinyl acetate production installation as follows. Two runs of such compressor were made before employing the hindered phenol antifoulant, which runs provided a base-line for assessing the hindered phenol's performance. The adiabatic efficiency of the compressor during these runs was monitored. The first run was started on day-1, at which time the compressor was freshly cleaned, and terminated on day-43, after which it was recleaned. The second run was started on day-44 and terminated on day-123. The untreated runs therefor lasted 43 and 80 days of continuous vinyl acetate production. A third run, also with a freshly cleaned compressor, but adding the hindered phenol in an acetic acid diluent to the compressor feed, at a dosage within the range of from about 10 to about 50 ppm based on phenol actives, started on day-124 and the adiabatic efficiency monitoring, but not the run, terminated on day-192. The dosage of hindered phenol, while within the above-noted range, was not constant over the day-124 to day-192, but the treatment at dosages of at least 10 ppm was continuous over that time period. Over the course of the first run, the adiabatic efficiency decreased from 72.5% to 61.5%, which was an 11 percentage point reduction over 43 days, or an average of 0.26 percentage points per day. Over the course of the second run, the adiabatic efficiency decreased from 74.5% to 53%, which was an 21.5 percentage point reduction over 80 days, or an average of 0.27 percentage points per day. Over the course of the third run, the adiabatic efficiency decreased from 75% to 63%, which was an 12 percentage point reduction over 69 days, or an average of 0.17 percentage points per day. In comparison to the first run, as a base-line, the treatment of the present invention extended the time period in which similar levels of adiabatic efficiencies were reached by 26 days, or 60 percent. In comparison to the second run, as a base-line, the treatment of the present invention reduced the average drop in adiabatic efficiency (measured in percentage points based on percentage differentials) by about 37 percent ((0.27−0.17)/0.27×100). In addition, during all three runs the compressor flow speed, which is another measure of compressor efficiency, was monitored. In FIG. 1 there is shown a plot of the compressor volume flow per rpm versus the passage of time during the time period encompassing all three of these runs. The compressor flow rate ("VOL. FLOW/RPM") is given in terms of MSCFH/RPM (described above). The plot segments corresponding to each run are seen in FIG. 1 as three distinct sets of data points, each set sketching a downward slope versus time. The average slope of the third run set of data points is clearly seen as less than the average slopes of the first two base-line runs.

EXAMPLE 2

A solution of 2,6-di-tert-butyl-4-nonylphenol in acetic acid was prepared, stored at ambient room temperature for a time period of about 127 days, and then analyzed together with a freshly made sample by $^1$HNMR and $^{13}$CNMR, which demonstrated that no significant chemical changes occurred during such aging period despite the presence of the acetic acid.

EXAMPLE 3

A solution of 2,6-di-tert-butyl-4-nonylphenol in a heavy aromatic solvent was determined to have a vapor pressure of <2.5 mm Hg at both 100° F. and 135° F., which is considered negligible, the vapor pressure instrumentation accurately reading down only to 2.5 mm Hg.

The present invention provides a method for reducing the fouling of a compressor of a vinyl acetate production unit having a light ends stream feed. The present method is also a method for treating a light ends stream of a vinyl acetate production system upstream of a compressor feed point so as to retard the loss of compressor efficiency with run time by reducing the fouling of the compressor. The invention also provides method whereby the run time of a light ends stream compressor before clean-out is required is increased by inhibiting or reducing the fouling of the compressor. The method(s) is comprised of adding to the compressor feed or light ends stream a hindered phenol in a dosage amount effective for reducing the fouling of the compressor.

In preferred embodiment the hindered phenol is added at a dosage of from about 1 ppm to about 500 ppm, and more preferably at a dosage of from about 5 ppm to about 200 ppm. For most compressors in preferred embodiment the hindered phenol is added at a dosage of from about 10 ppm to about 100 ppm.

The hindered phenol in preferred embodiment has a structure of Formula I above, wherein R' is a linear or branched chain alkyl having at least 3 carbons and mixtures thereof, R" is hydrogen or a linear or branched alkyl and mixtures thereof, provided that together R' and R" are comprised of no more than about 12 carbons, and R is hydrogen or linear or branched, saturated or unsaturated alkyl having from one to about 28 carbon atoms and mixtures thereof.

In more preferred embodiments: both R' and R" are alkyls each having at least about 3 carbons and mixtures thereof: R' and R" together contain no more than about 10 carbons; R is an alkyl having from about 1 to about 22 carbons and mixtures thereof; R is an alkyl having from about 6 to about 22 carbons and mixtures thereof; R' and R" are independently (iso)propyl, (iso/tert)butyl, or mixtures thereof; and R' and R" are independently a linear or branched chain alkyl having from about 3 to about 4 carbons and mixtures thereof, and R is a linear or branched, saturated or unsaturated alkyl having from about 6 to about 12 carbon atoms and mixtures thereof. In another preferred embodiment, the hindered phenol is 2,6-di-tert-butyl-4-nonylphenol, including any and all isomers thereof.

INDUSTRIAL APPLICABILITY OF THE INVENTION

The present invention is applicable to the vinyl acetate production industry.

We claim:

1. A method for treating a light ends stream of a vinyl acetate production system upstream of a compressor feed point so as to retard the loss of compressor efficiency with run time by reducing the fouling of said compressor comprising:

adding to said light ends stream a hindered phenol at a dosage of from about 1 ppm to about 500 ppm: and wherein said hindered phenol is 2,6-di-tert-butyl-4-nonylphenol.

2. A method whereby the run time of a light ends stream compressor before clean-out is required is increased by inhibiting or reducing the fouling of the compressor, wherein the compressor feed is a light ends stream, comprising:

adding to said compressor feed a hindered phenol at a dosage of from about 5 ppm to about 200 ppm;

wherein said hindered phenol is 2,6-di-tert-butyl-4-nonylphenol.

* * * * *